United States Patent
Mizutani et al.

(10) Patent No.: US 7,969,569 B2
(45) Date of Patent: Jun. 28, 2011

(54) METHOD FOR DETECTING TRACE SUBSTANCE USING ORGANIC ELECTROLUMINESCENT DEVICE

(75) Inventors: Wataru Mizutani, Ibaraki (JP); Kiyomi Tsukagoshi, Ibaraki (JP); Koichi Sakaguchi, Ibaraki (JP); Yuuji Yoshida, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 267 days.

(21) Appl. No.: 12/445,617

(22) PCT Filed: Oct. 15, 2007

(86) PCT No.: PCT/JP2007/070090
§ 371 (c)(1),
(2), (4) Date: Apr. 21, 2009

(87) PCT Pub. No.: WO2008/047762
PCT Pub. Date: Apr. 24, 2008

(65) Prior Publication Data
US 2010/0039647 A1    Feb. 18, 2010

(30) Foreign Application Priority Data
Oct. 16, 2006    (JP) .................................. 2006-281631

(51) Int. Cl.
*G01N 21/00*    (2006.01)

(52) U.S. Cl. ...... 356/300; 356/218; 436/164; 435/288.7
(58) Field of Classification Search .................. None
See application file for complete search history.

(56) References Cited

U.S. PATENT DOCUMENTS

| | | | |
|---|---|---|---|
| 5,936,730 A | 8/1999 | Foley et al. | |
| 6,331,438 B1 | 12/2001 | Aylott et al. | |
| 6,767,733 B1 | 7/2004 | Green | |
| 2005/0019947 A1 | 1/2005 | Ito et al. | |
| 2005/0181380 A1 | 8/2005 | Isobe | |

FOREIGN PATENT DOCUMENTS

| | | |
|---|---|---|
| JP | 07-012730 A | 1/1995 |
| JP | 08-029330 A | 2/1996 |
| JP | 08-050096 A | 2/1996 |
| JP | 10-197526 A | 7/1998 |

*Primary Examiner* — F. L Evans
(74) *Attorney, Agent, or Firm* — Howson & Howson LLP (57) ABSTRACT

Provided is a detection method and device for analyzing trace substance of interest in a short time and with high accuracy without the need of performing any treatment for binding a fluorescent substance to the substance of interest or using any large apparatus. The substance of interest is detected by being immobilizing on a surface of any one of a hole transport layer, an electron transport layer, a luminescent layer, a buffer layer, and inside surfaces of electrodes for an organic electroluminescent device based on a change in at least one luminescent property selected from luminescence intensity, luminous efficiency, and emission spectrum of the organic electroluminescent device before and after the immobilization of the substance of interest.

12 Claims, 7 Drawing Sheets

Fig.1

Luminescence

METHOD FOR DETECTING TRACE SUBSTANCE USING ORGANIC ELECTROLUMINESCENT DEVICE

TECHNICAL FIELD

The present invention generally relates to a method and device for detecting trace substance such as environmental pollutants or biomaterials with high sensitivity, and more particularly, to a method and device for detecting trace substance using an organic electroluminescent device.

BACKGROUND ART

In order to identify and detect protein molecules such as enzymes or antibodies, or biomolecules such as DNA or sugar chains, in a short time with accuracy and efficiency, a method of using a substrate on which a substance such as an antigen or antibody that will be specifically bonded to a substance of interest is directly or indirectly immobilized, making the substance of interest labeled with a fluorescent substance flow over the substrate, then irradiating the substrate with an excitation light to make the fluorescent substance used as the label to emit, and thereby detecting the substance of interest specifically bonded to the above-described substance, based on either presence or absence of the light, is currently used. A technique of using an organic luminescent dye, in substitute for an expensive and exclusive fluorochrome, as the fluorescent substance is known (see Patent Document 1). A technique of using an organic electroluminescent device as an excitation light source to make the above-mentioned fluorescent substance to emit is also known (see Patent Documents 2 to 5).

However, with the conventional technique using a fluorochrome, it takes time and effort to prepare and bond the fluorochrome to object molecules, and a detection device including an excitation light source appropriate to the relevant dye and detection optical filters appropriate to the relevant fluorescence wavelength are required. Therefore, an easy detection method without use of the fluorochrome is needed. Furthermore, in relation to the typical method for detecting the biomaterials or like mentioned above, a technique of easily monitoring the health condition of people at home is needed with the rapid aging of society and, therefore, various biochips have been developed. In a case where an organic electroluminescent device is used as a light source, the problem specific to the fluorescence detection method remains, because treatment for bonding a fluorochrome to object molecules and a detection device are needed.

[Patent Document 1] Japanese Patent Application Laid-Open Publication No. 2005-208026
[Patent Document 2] Japanese Patent Application Laid-Open Publication No. H10-197526
[Patent Document 3] Japanese Patent Application Laid-Open Publication No. H8-29330
[Patent Document 4] U.S. Pat. No. 6,767,733
[Patent Document 5] U.S. Pat. No. 5,936,730

DISCLOSURE OF THE INVENTION

The present invention was devised in light of the circumstances described above. Thus, an object of the invention is to provide a detection method for analyzing trace substance of interest in a short time with high accuracy without the need of performing any treatment for binding a fluorescent substance to the substance of interest or using any large apparatus, and a device for the above-described detection method.

After intense study to achieve the above-described object, the inventors of the present invention have found that the above-described object can be achieved by using an organic electroluminescent device, not as an excitation light source, but directly as a detection sensor, of which application to thin displays or the like has recently drawn attention.

Specifically, the organic electroluminescent device typically has a multilayered structure constituted from electrodes and layers placed between the electrodes such as a hole transport layer, a luminescent layer, and an electron transport layer. It is known that contamination of the organic electroluminescent device by impurities during the manufacturing process may cause deterioration such as quenching and decrease in luminance due to the operation environment. This is a serious problem that should be overcome for applying to displays, however, the inventors have found that the object molecules can be detected using such a quenching phenomenon that may occur when biomolecules or the like of interest are sandwiched inside the layered structure of an organic electroluminescent device as described above, and the organic electroluminescent device can thereby be utilized as a highly sensitive detection element.

The present invention was completed based on the above-described finding and through thorough examinations, and provides:

(1) A detection method characterized in that a substance of interest is immobilized on a surface of any one of layers existing between opposite electrodes of an organic electroluminescent device, and the substance of interest is detected based on a change in at least one luminescent property selected from luminescence intensity, luminous efficiency, and emission spectrum of the organic electroluminescent device before and after the immobilization of the substance of interest.

(2) The detection method according to (1), characterized in that the surface is any one of a hole transport layer surface, an electron transport layer surface, a luminescent layer surface, a buffer layer surface, and an inside surface of an electrode layer in the organic electroluminescent device.

(3) The detection method according to (1) or (2), characterized in that not less than two kinds of substances of interest are immobilized at different positions on the surface.

(4) The detection method according to any one of (1) to (3), characterized in that a surface treatment is applied to the surface so that only the substance of interest is immobilized on the surface.

(5) A detection device characterized in that it comprises an organic electroluminescent device; a layer existing between opposite electrodes of the organic electroluminescent device and having a surface on which a substance of interest is immobilized; and means for measuring a change in at least one luminescent property selected from luminescence intensity, luminous efficiency, and emission spectrum of the organic electroluminescent device before and after the immobilization of the substance of interest.

(6) The detection device according to (5) above, characterized in that the layer on which the substance of interest is immobilized is any one of a hole transport layer, an electron transport layer, a luminescent layer, a buffer layer, and an electrode layer in the organic electroluminescent device.

(7) The detection device according to (5) or (6) above, characterized in that at least two kinds of substances of interest are immobilized at respectively different positions on the surface of the layer.

(8) The detection device according to any one of (5) to (7) above, characterized in that a treatment is applied to the surface so that only the substance of interest is immobilized on the surface of the layer.
(9) A protein detection chip including an organic electroluminescent device; and a layer existing between opposite electrodes of the organic electroluminescent device and having a surface on which a protein of interest is immobilized.
(10) The protein detection chip according to (9) above, characterized in that the layer on which the protein of interest is immobilized is any one of a hole transport layer, an electron transport layer, a luminescent layer, a buffer layer, and an electrode layer in the organic electroluminescent device.
(11) The protein detection chip according to (9) or (10) above, characterized in not less than two kinds of proteins of interest are immobilized at respectively different positions on the surface of the layer.
(12) The protein detection chip according to any one of (9) to (11) above, characterized in that a treatment is applied to the surface so that only the protein of interest is immobilized on the surface of the layer.

EFFECT OF THE INVENTION

According to the present invention, a substance can be detected visually or with a photosensitive element such as a CCD, by emission caused by connecting a luminescent device to a power source of several volts that can be easily provided using dry cell batteries or like, without the need to use pilot dyes or an excitation light source. Furthermore, additional information for use in identifying the detected substance can be obtained; for instance current properties specific to the molecules placed between the layers in the luminescent device and an emission spectrum different from that of an element with no molecules placed between its layers.

DESCRIPTION OF REFERENCE NUMERALS a: upper electrode
b: electron transport layer
c: luminescent layer
d: hole transport layer
e: buffer layer
f: transparent electrode
g: protein molecules
h: Alq3 molecule layer also serving as the electron transport layer b and the luminescent layer c
A: electrode terminal block for measuring
B: glass substrate on which three organic EL cells are manufactured
C: luminescent area
D: upper electrode
E: transparent electrode
F: cell with the luminescent layer on which a BSA pattern thin film is formed by mCP
G: cell with Cyt. C formed on its entire surface
1: organic EL multilayered lower structure
2: area where only protein molecules A (●) are adsorbed
3: area where only protein molecules B (▲) are adsorbed
4: area where no protein molecule will be adsorbed
5: organic EL multilayered upper structure
6: organic EL multilayered upper structure
7: organic EL multilayered lower structure
8: substance of interest
9: specific adsorption site
10: temporary substrate
11: polymer
12: upper electrode
13: tape
14: ITO/glass
15: polymer
16: detection unit
17: electrode
18: power source unit
19: switch

BEST MODE FOR CARRYING OUT THE INVENTION

Figure 1:
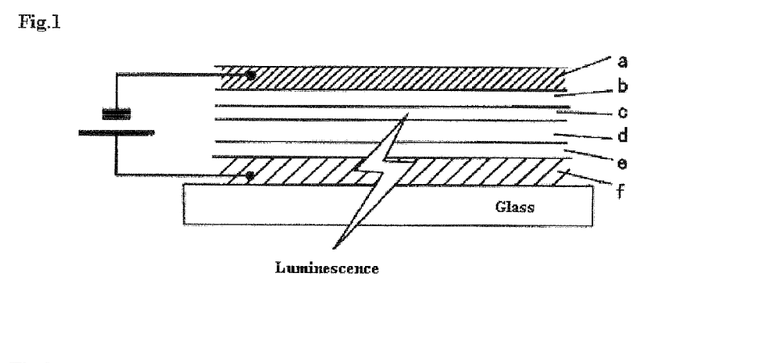
FIG. 1 is a diagram illustrating the layered structure of a typical organic EL device.

Preferred embodiments of the present invention are now explained with reference to the attached drawings.
FIG. 1 is a diagram illustrating the layered structure of an organic electroluminescent device (hereinafter referred to the "organic EL device"). As shown in FIG. 1, a typical organic EL device is constituted from an upper electrode (a) also serving as a reflective layer, an electron transport layer (b), a luminescent layer (c), a hole transport layer (d), a buffer layer (e), and a transparent electrode (f), all of which are constructed on a glass substrate. In the above-described layered structure, one layer may also serve as another layer; for example, the electron transport layer may serve as the luminescent layer. Therefore, the minimum layered structure of the organic EL device is a single-layer structure in which the luminescent layer is placed between two electrodes, at least one of which is transparent.

Based on the method and according to the invention, trace substance is detected by being immobilizing on the surface of any one of constituent layers existing between the two electrodes of the organic EL device; that is, on the surface of any one of the hole transport layer (d), the electron transport layer (b), the luminescent layer (c), or the buffer layer (e), or the inside surface of the electrode (a), (f) (the under surface of (a) or the upper surface of (f)), and then by letting luminescent properties of the organic electroluminescent device, such as the luminescence intensity, luminous efficiency, and emission spectrum, change before and after the immobilization of the substance of interest.

Each of the above-mentioned constituent layers itself is constituted from a plurality of layers, and the substance of interest may be immobilized between these plurality of layers.

Furthermore, a layer, other than the preceding constituent layers of the organic EL device, for immobilizing the substance of interest may be added and inserted between the two electrodes of the organic EL device, and the substance of interest may be immobilized on the surface of that additional layer.

When the substance detected by the method and device according to the invention is spherical, the substance with a diameter may range from several nanometers to 100 nm; and when the substance detected by the method and device according to the invention is linear, the substance with the cross-sectional size may range from several nanometers to 100 nm. Specific examples of the substance of interest include protein molecules such as enzymes and antibodies, biomolecules such as DNA and sugar chains, carbon-based nanoparticulates such as fullerene and carbon nanotubes, and environmental pollutants such as diesel particulates and asbestos.

Since the substance(s) of interest described above is immobilized on the surface of any one of the hole transport layer, the electron transport layer, the luminescent layer, the buffer layer of organic EL Device, and the inside surface of the electrodes, for the purpose that only the specified substance can be selectively detected, it is preferable to apply surface treatment to the above-mentioned surface so that only the specified substance(s) and no other substances, can be attached to the surface.

Specific examples of thin films to which the surface treatment is applied include: thin films of poly(ethylene glycol) or phosphorylcholine that inhibits nonselective adsorption of antibody molecules, which are bonded only to specified protein molecules, or protein molecules; a single-layer, self-assembled molecule film composed of molecules having a similar function to that described above; and combinations of the above-listed films.

The surface treatment described above should preferably be applied to a single molecule film or any thin film similar thereto and an influence of the surface treatment on the luminescent properties should preferably be less than a change in the luminescent properties caused by the substance of interest.

Furthermore, two or more different kinds of substances of interest can be detected based on a change in the luminescent properties by immobilizing them at different positions on the surface of any one of the hole transport layer, the electron transport layer, the luminescent layer, the buffer layer, and the inside surface of the electrodes in the organic EL device.

If the plurality of substances of interest is immobilized, the following configurations are possible; a configuration where a pair of electrodes simultaneously applies a voltage to the positions where the substances of interest are immobilized, and a configuration where electrodes that are insulated from each other are constructed and a voltage is applied to the electrodes separately. With the latter configuration, it is possible to measure not only the luminescence intensity and the spectrum but also the individual current-luminous efficiency. Thus, the latter configuration is favorable because useful information to identify the substances of interest can be obtained.

Furthermore, a protein detection chip for detecting at least two different kinds of protein molecules by using a change in the luminescent properties can be obtained by applying a surface treatment to the relevant layer surface of the organic EL device so that the at least two different kinds of protein molecules are immobilized at different positions on the surface of any one of the hole transport layer, the electron transport layer, the luminescent layer, the buffer layer, and the inside surface of the electrodes in the organic EL device.

Figure 2:
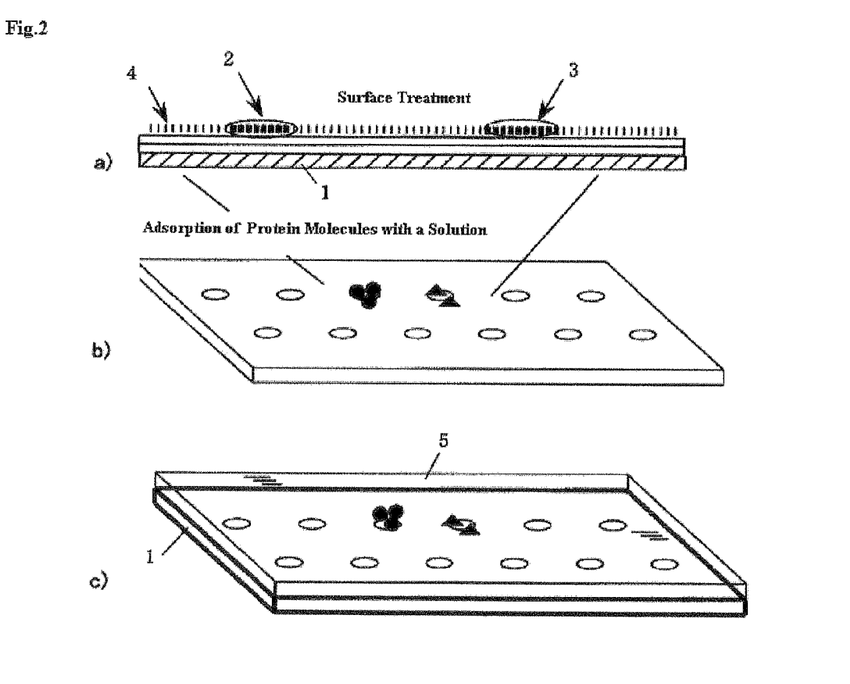
FIG. 2 is a diagram illustrating the outline of a surface treatment necessary for a protein chip for detecting a plurality of protein molecules.

FIG. 2 is a diagram illustrating the outline of an example of a process for manufacturing a protein chip for detecting a plurality of protein molecules at the same time.

FIG. 2a shows that an area (2) to which a treatment has been applied to make a lower structure (1) of the multilayered structure of the organic EL device adsorb only protein molecules A (●), and an area (3) to which a treatment has been applied to make the lower structure (1) adsorb only protein molecules B (▲) are provided and a treatment has been applied to the remaining area (4) so that the area (4) will not adsorb the protein molecules.

FIG. 2b shows the state where the surface to which the above-described treatments were applied has adsorbed the protein molecules A (●) and the protein molecules B (▲), which are the substances of interest, by making a solution containing the protein molecules A and the protein molecules B in contact with the surface.

FIG. 2c shows that the remaining layered structure (5) for the organic EL device has been added to and piled on the surface obtained in FIG. 2b.

In order to immobilize the substance(s) of interest on the surface of any one of the hole transport layer, the electron transport layer, the luminescent layer, the buffer layer, and the inside surface of the electrodes, all of which configure the inside of the organic EL device, as described above, it is necessary to make the substance(s) of interest in contact with the surface in the middle of the process for manufacturing the organic EL device.

Specifically, if the substance of interest is an environmental pollutant suspended in the atmosphere, the surface of any one of the hole transport layer, the electron transport layer, the luminescent layer, the buffer layer, and the inside surface of the electrodes, all of which configure the inside of the organic EL device, are exposed to gas containing substance of interest for a certain period of time, and then the missing layered structure of the organic EL device is added to the above surface, thereby configuring the detection device.

With the substance of interest being a biomaterial contained in a solution a detection apparatus is configured by a procedure that the solution is made in contact with the surface of any one of the hole transport layer, the electron transport layer, the luminescent layer, the buffer layer, and the inside surface of the electrodes, all of which configure the inside of the organic EL device, by a method such as ink-jet printing, micro-contact printing, or casting, and then the surface is rinsed, if necessary, in order to remove any substances other than the object substance of interest, and finally the missing layered structure of the organic EL device is added to the above surface, thereby obtaining the detection device.

With the above-described process, it is preferable that a treatment such as filtering is performed beforehand so that the gas or solution containing the substance of interest will not contain any substance other than the object substance of interest, which would influence the luminescent properties.

Furthermore, the surface on which the substance of interest being immobilized should preferably be treated as described above so that it will selectively adsorb only the object substance of interest, and will not adsorb any other substances.

The layered structure constituting the organic EL device can be made by the use of known methods.

The layered structure can be made by, for example, the following processes: wet processes such as a printing process, spin coating, dip coating, and casting; physical processes such as vacuum deposition, sputtering, and ion plating; and chemical processes such as CVD and plasma CVD.

As a method for adding the organic EL layered structure onto the surface where the substance of interest is immobilized, it is possible to prepare the necessary layered structure in a flexible film by any of the aforementioned processes in advance and then make the surface and the layered structure in physical contact with each other (bonded to each other), thereby configuring the organic EL device.

Figure 3:
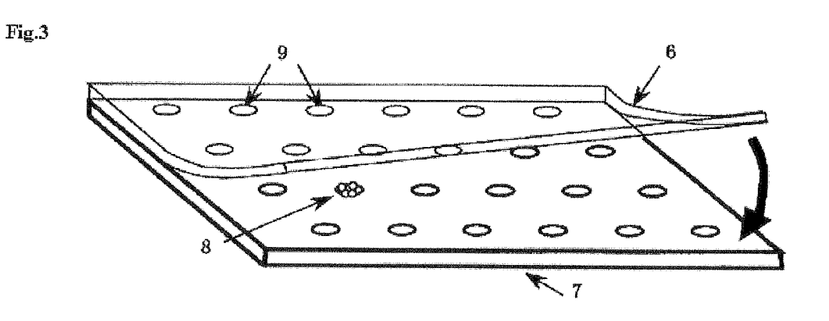
FIG. 3 is a diagram illustrating the outline of a lamination method, which is one of the methods for placing an object substance between layers of the organic EL device multilayered structure.

FIG. 3 shows a lamination method which is one of the methods of placing the object substance between layers in the organic EL multilayered structure. Regarding reference numerals in FIG. 3, "6" represents an organic EL multilayered upper structure made of a polymer film or the like, "7" represents an organic EL multilayered lower structure, "8" represents a substance of interest, and "9" represents specific adsorption sites, respectively.

As shown in FIG. 3, the lamination method is used after preparing an upper portion and a lower portion of the multilayered structure of the organic EL device separately, and immobilizing the object substance on the surface of the lower structure, to physically bond the upper multilayered structure, which includes the flexible polymer film as a base, to the lower structure, thereby configuring the organic EL device.

An example of a detection device according to the present invention, using the above-described lamination method, as well as a detection method using such a detection device will be explained below with reference to the relevant drawings.

Figure 4:
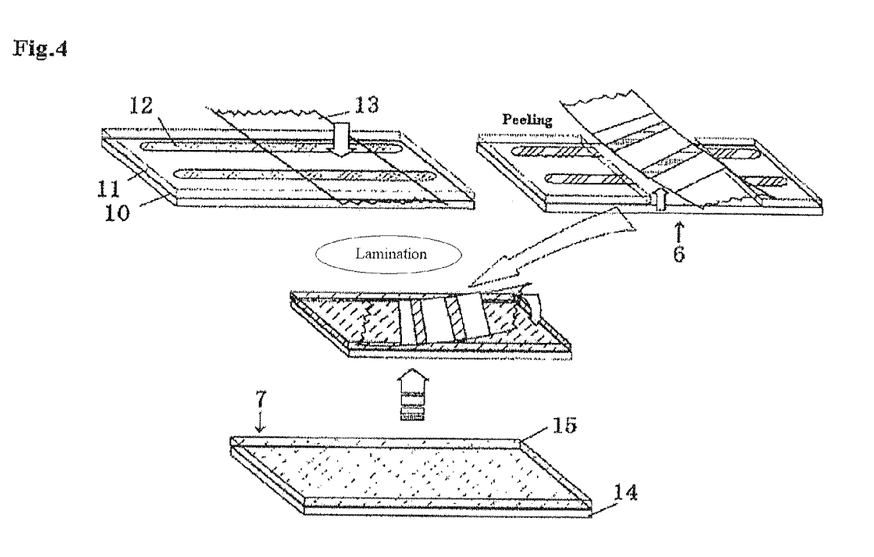
FIG. 4 is a diagram illustrating the outline of a detection device using the lamination method, and a detection method using the above-mentioned detection device.

As shown in FIG. 4, the upper structure (6) for the organic EL device is made by using polytetrafluoroethylene (PTFE) as a temporary substrate (10), spin-coating the temporary substrate (10) with a poly[2-methoxy-5-(2'-ethyl-hexylixy)-1,4-phenylene vinylene] (PPV) 0.3% chloroform solution or a poly(9,9-dioctylfluorene-2,7-diyl) (PFO) 0.5% chloroform solution, both of which are representative polymeric luminescent materials, to form a film (11), and then forming an aluminum upper electrode (12) on the film (11) by means of vacuum deposition. After a mending tape (13) for office use is attached to the film structure on the temporary substrate, the film structure together with the tape can be easily removed from the temporary substrate.

On the other hand, the lower structure (7) is made by forming a Poly(3,4-ethylenedioxythiophene) (PEDOT) thin film, by means of spin-coating, on a glass substrate (14) on which a transparent electrode made of indium tin oxide (ITO) is formed, and then forming a PPV film or a PFO film (15) on the PEDOT thin film, using the above-mentioned PPV or PFO toluene solution in the same manner as described above.

After the substance of interest is immobilized on the PPV film or PFO film (15) constructed above, the polymer film with the electrode on the tape removed from the temporary substrate is bonded to the lower structure, and the respective electrodes of the upper and lower structures are connected to a power source; and as a result, luminescence can be observed through the ITO/glass (14).

Figure 5:
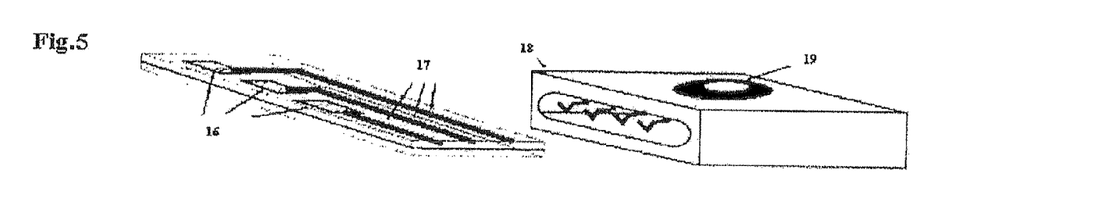
FIG. 5 is a schematic diagram of an example of devices for detecting the luminescence intensity using the organic EL device according to the present invention.

FIG. 5 is a schematic diagram illustrating an example of a device for detecting the luminescence intensity using the organic EL device according to the present invention.

Regarding reference numerals in FIG. 5, "16" represents detection units, "17" represents electrodes, "18" represents a power source unit, and "19" represents a switch, respectively.

As shown in FIG. 5, when the detection units (16) for the organic EL device on which substances of interest are immobilized are inserted into the power source unit (18), the detection units emit, and an intensity difference can be checked and observed by pressing the switch (19).

EXAMPLES

The present invention is now explained below in further detail based on examples. However, the invention is not limited to these examples.

Incidentally, a molecule layer and electrodes were manufactured by vacuum deposition in the examples described below in order to obtain basic data for checking the effect of protein molecules, which were placed between layers in the organic EL device, on luminescent properties. For practical purposes, however, the molecule layer and the electrodes can be manufactured without using a vacuum device, by either a method of immobilizing protein molecules or the like in advance, followed by applying a solution of constituent molecules to the upper element structure; or by a method as shown in FIG. 3 or FIG. 4 of the upper structure being prepared in a flexible sheet in advance, followed by lamination.

Example 1

Figure 6:
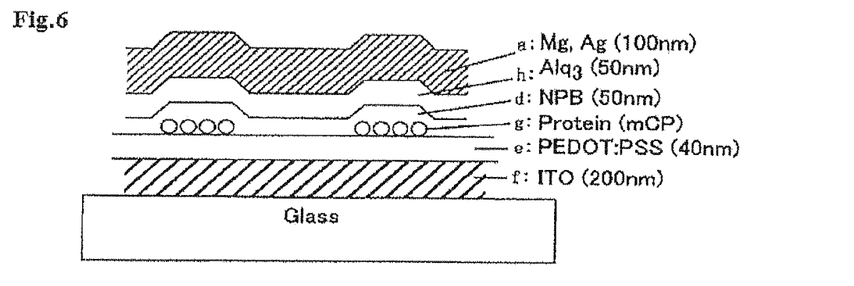
FIG. 6 is a diagram illustrating the structure of a detection device manufactured in Example 1.

FIG. 6 shows the structure of the manufactured detection device.

In this example, a transparent electrode (f) (200 nm) film made of indium tin oxide (ITO) was formed on a glass substrate by means of sputtering, and wet etching was performed to form into lines, each of which was 2 mm wide.

Next, the transparent electrode (f) was spin-coated with a buffer layer (e) (40 nm) made of poly(3,4-ethylenedioxythiophene) poly(styrenesulfonate) (PEDOT/PSS), and protein molecules (g) were then patterned on the buffer layer by means of micro-contact printing (mCP).

For the mCP of the protein molecules, a 0.4 mg/ml solution in a case of bovine serum albumin (BSA) or a 0.5 mg/ml solution in a case of electron transferring proteins (Cyt. C) was used. After a stamp made of polydimethylsiloxane (PDMS) was immersed in the above-described solution for 40 minutes and made to adsorb the relevant substance, the excess solution was rinsed off with pure water and the stamp was dried, and then was made in contact with the object surface for three minutes.

N,N-di(naphthalene-1-yl)-N,N-diphenyl-benzidene (NPB) (50 nm) as a hole transport layer (d) and a molecule layer of aluminate-tris-8-hydroxyquinolate (Alq3), which is aluminum quinoline, (h) (50 nm) serving also as an electron transport layer (b) and a luminescent layer (c) were vacuum-deposited on the above-obtained layers, and then Mg and Ag were co-deposited as upper electrode metals (a) (100 nm) on the molecule layer (h) by means of vacuum deposition.

Figure 7:
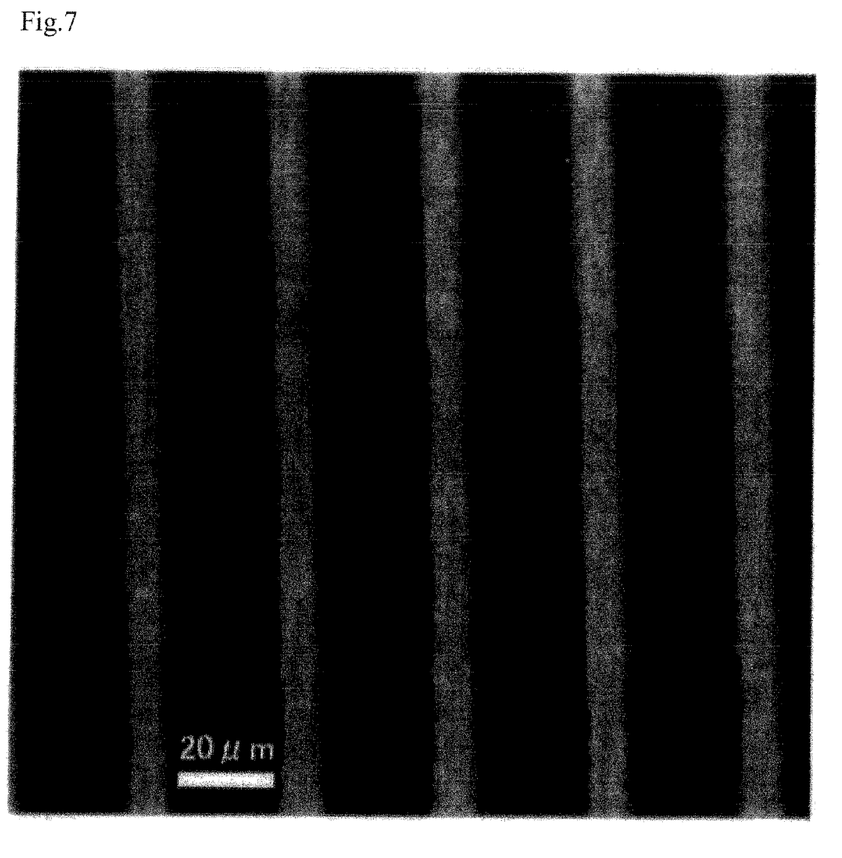
FIG. 7 shows a luminescent pattern of the organic EL device that reflects protein molecules patterned in lines.
Figure 8:
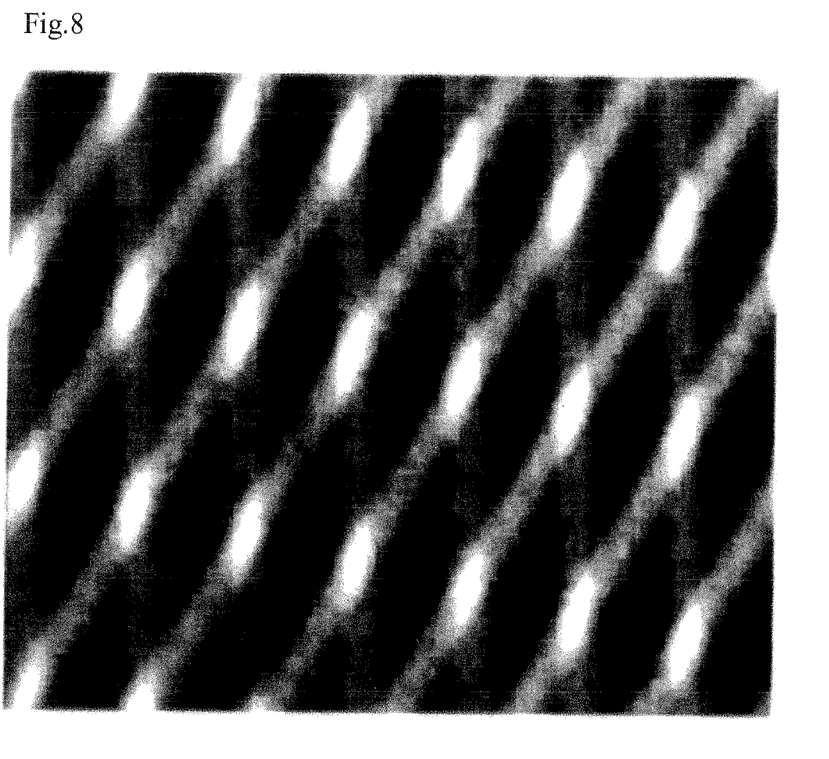
FIG. 8 shows a grid-like luminescent pattern obtained by performing patterning twice at different angles.
Figure 9:
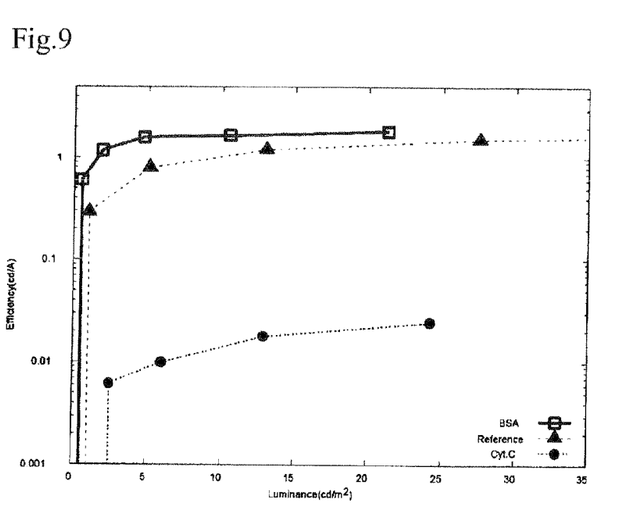
FIG. 9 shows the relationship between the type of protein molecules and current efficiency.

The detection results obtained using the device of the above-described example is shown in FIGS. 7 to 9.

The voltage and luminance were measured using an electrometer (Keithley 2400) and a luminance meter (Topcon BM-9). The EL emission spectrum was measured with a CCD multi-channel spectroscope (Hamamatsu Photonics K.K) via optical fibers. Luminescent patterns were observed using a microscope (ZEISS Axiovert 135). All the measurements were conducted in the atmosphere at room temperature.

FIG. 7 shows the results of observation of the luminescent pattern using the device of Example 1. It shows that the low luminescence intensity at protein molecule (bovine serum albumin (BSA)) portion which is patterned in lines. As a result of measurement with an atomic force microscope (AFM), there was not more than one protein molecule layer that was manufactured by mCP.

FIG. 8 shows a grid pattern obtained as a result of printing twice at different angles. It shows differences in the luminescence intensity depending on the density of the protein molecules.

The above-described results, with the use of the detection method and device of the present invention, show not only presence or absence of the substance of interest, but also a concentration of the substance of interest.

FIG. 9 is a chart showing different current efficiencies depending on the kinds of protein molecules.

In FIG. 9, the line with mark "-▲-" is plotted to show dependency of luminous efficiency of an organic EL device for reference, which contains no excess molecules placed between its layers, on luminescence intensity; the line with mark "-□-" is plotted to show the case where bovine serum albumin (BSA) is placed between the layers of the organic EL device; and the line with mark "-●-" is plotted to show the case where electron transferring proteins (cytochrome C (Cyt. C)) are placed between the layers of the organic EL device.

As is apparent from this drawing, if the cytochrome C which is protein molecules having the electron transfer system is placed between the layers of the organic EL device, the current necessary to obtain the same luminescence intensity increases and the efficiency decreases. On the other hand, if the bovine serum albumin (BSA) which is the protein molecules having insulation properties is placed between the layers of the organic EL device, the luminous efficiency increases.

The above results, with the use of the detection method and device of the present invention, show that the substances of interest can be identified based on differences in the current effect of each substance of interest.

Example 2

Observations of an emission spectrum at high bias voltage were conducted on an element in which transferrin, one type of protein molecules, was immobilized was manufactured in Example 2 in the same manner as in Example 1.

Figure 10:
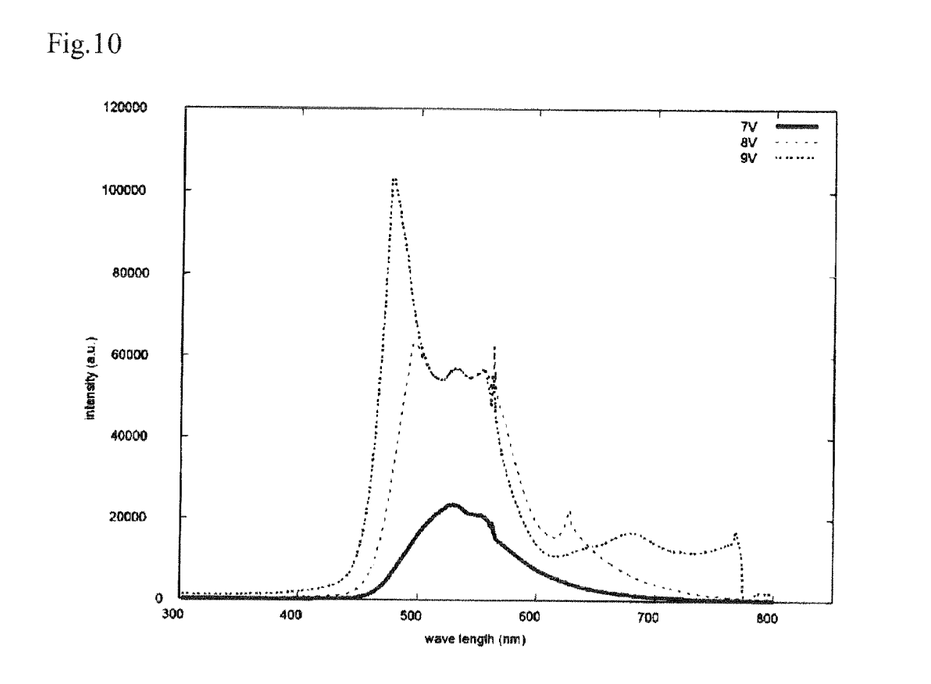
FIG. 10 shows the relationship between a bias voltage and an emission spectrum.

FIG. 10 shows the results thereof. A solid line, a dotted line, and a dashed line in FIG. 10 represent emission spectrums when the bias voltage was 7V, 8V, and 9V, respectively.

As is apparent from FIG. 10, the emission spectrum at 7V is similar to that of an ordinary organic EL device; however, at about 8V and higher, the peaks appear on the short wavelength side and the long wavelength side. When the voltage is increased, the peak on the long wavelength side is further shifted toward the longer wavelength.

The-above-described shift of the peak in the emission spectrum toward the short wavelength side or toward the long wavelength side when a high bias voltage is applied to the organic EL device is attributable to the electronic state of the protein molecule thin film. Therefore, detection of the electronic state of the protein molecule thin film will be a clue to identify the substance of interest.

Example 3

In this example, detection devices in which protein molecules were placed between layers different from those in Example 1 were manufactured. The reference symbols in FIG. 11 the same as those shown in FIG. 6 represent the same elements as in FIG. 6.

Figure 11:
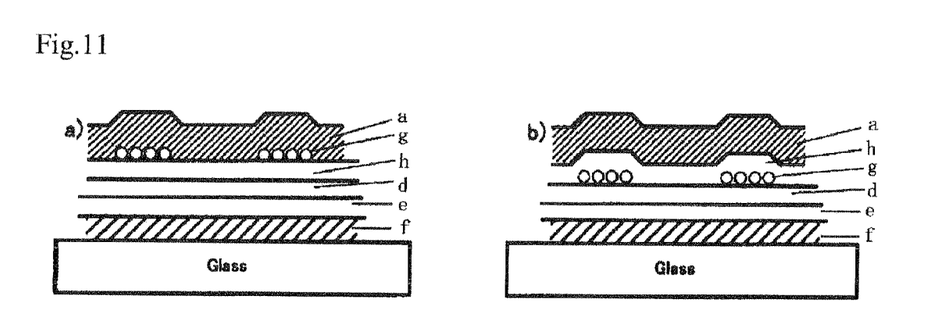
FIG. 11 shows the structures of detection devices in which a substance of interest is immobilized between layers different from those in Example 1.

FIG. 11a shows that the protein molecules (g) were stamped after deposition of the Alq3 layer (h), and then the upper electrode (a) was formed on the protein molecules (g). Similarly, FIG. 11b shows that the protein molecules (g) were stamped between the NPB layer (d) and the Alq3 layer (h).

In this example, a change in the luminescence intensity was observed in both the structures of FIG. 11a and FIG. 11b in the same manner as with the structure shown in FIG. 6.

Figure 12:
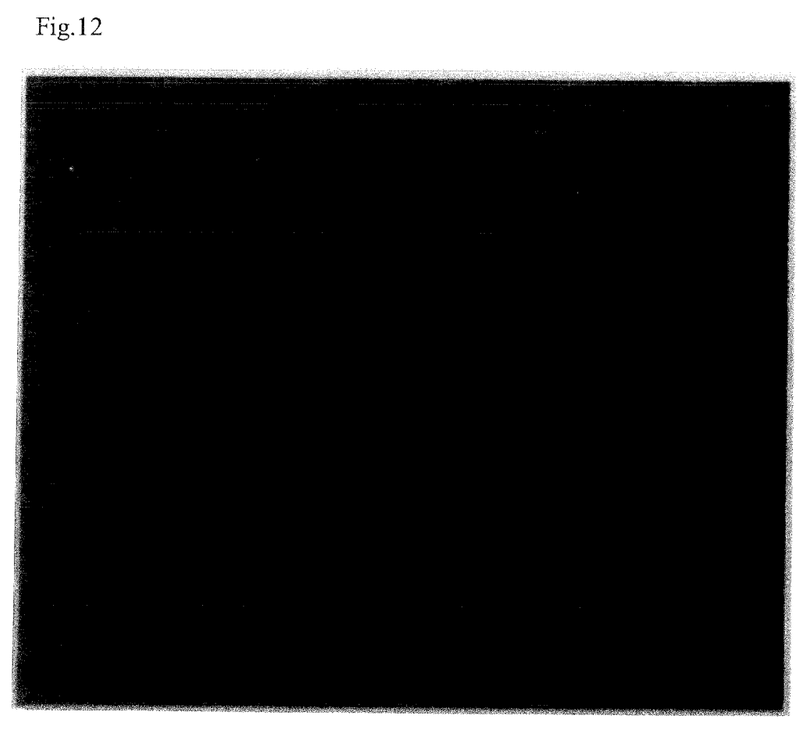
FIG. 12 shows a luminescent pattern of the organic EL device that reflects protein molecules patterned in lines by the device shown in FIG. 11(b)

FIG. 12 shows the result of observation of a luminescent pattern with the device shown in FIG. 11b. FIG. 12 shows that the luminescent intensity lowers at the protein molecule (bovine serum albumin (BSA)) portion which is patterned in lines.

Example 4

Figure 13:
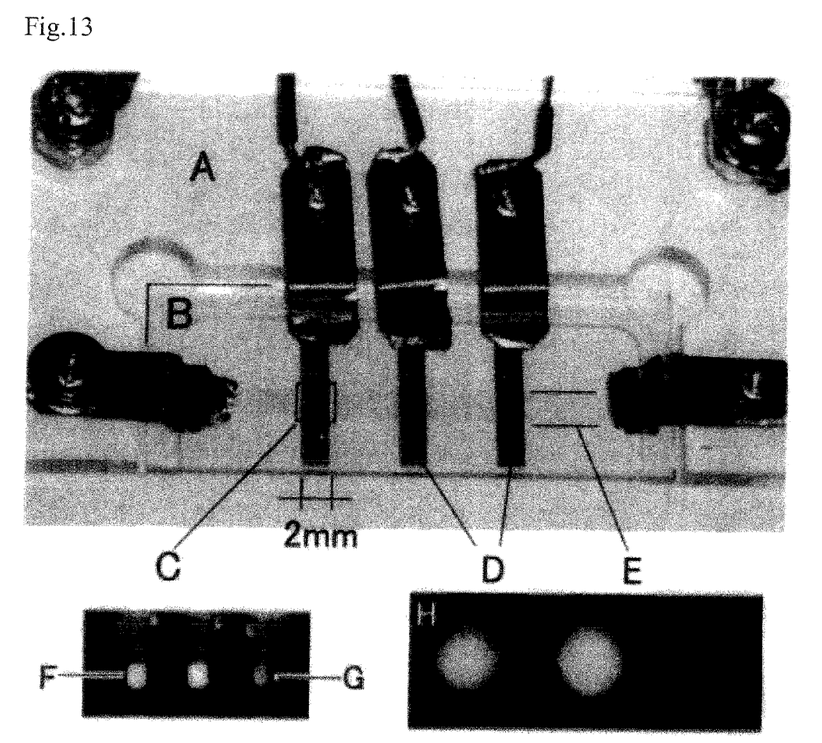
FIG. 13 shows an example in which a plurality of cells are manufactured on one substrate and are made to emit at the same time.

In this example, a plurality of cells were constructed on one substrate and made to emit at the same time as shown in FIG. 13. The structure shown in FIG. 11a was used for the organic EL device in this example.

Regarding reference symbols in FIG. 13, "A" represents an electrode terminal block for measurement, "B" represents a glass substrate on which three organic EL cells are constructed, and "C" represents a 2 mm×2 mm luminescent area located at the intersection of an upper electrode D and a transparent electrode E.

Luminescence was observed from the back side of the glass substrate. A diagram indicated below the above-described diagram in FIG. 13 shows the state where 5V was applied to the organic EL cells. "F" represents a cell in which a BSA pattern thin film was formed on the luminescent layer by means of mCP, "G" represents a cell on the entire surface of which Cyt. C was formed, and the cell in the middle is a reference cell in which no molecules were placed between the layers thereof.

"H" is a photograph taken in reduced illumination to compare the luminescence intensity between the cells. It is possible to visually recognize that the luminescence of the BSA cell is slightly darker than the reference cell in the middle and the luminescence intensity of the Cyt. C cell has lowered substantially as compared to the reference cell due to the influence of adsorption of the protein molecules.

INDUSTRIAL APPLICABILITY

The present invention enables to easily detect trace substance of interest whose size is about several nanometers to 100 nm, for example, protein molecules such as enzymes or antibodies, biomolecules such as DNA or sugar chains, carbon-based nanoparticulates such as fullerene or carbon nanotubes, or environmental pollutants such as diesel particulates or asbestos, without using pilot dyes or an excitation light source. Therefore, the invention can be used not only in the medical field, but also in the environmental field.

The invention claimed is:

1. A detection method characterized in that a substance of interest is immobilized on a surface of any one of layers existing between opposite electrodes of an organic electroluminescent device, and the substance of interest is detected based on a change in at least one luminescent property selected from luminescence intensity, luminous efficiency, and emission spectrum of the organic electroluminescent device before and after the immobilization of the substance of interest.

2. The detection method according to claim 1, characterized in that the surface is any one of a hole transport layer surface, an electron transport layer surface, a luminescent layer surface, a buffer layer surface, and an inside surface of an electrode layer in the organic electroluminescent device.

3. The detection method according to claim 1 or 2, characterized in that at least two kinds of substances of interest are immobilized at respectively different positions on the surface.

4. The detection method according to claim 1 or 2, characterized in that a surface treatment is applied to the surface so that only the substance of interest is immobilized on the surface.

5. A detection device characterized in that it comprises: an organic electroluminescent device; a layer existing between opposite electrodes of the organic electroluminescent device and having a surface on which a substance of interest is immobilized; and means for measuring a change in at least one luminescent property selected from luminescence intensity, luminous efficiency, and emission spectrum of the organic electroluminescent device before and after the immobilization of the substance of interest.

6. The detection device according to claim 5, characterized in that the layer on which the substance of interest is immobilized is any one of a hole transport layer, an electron transport layer, a luminescent layer, a buffer layer, and an electrode layer in the organic electroluminescent device.

7. The detection device according to claim 5 or 6, characterized in that at least two kinds of substances of interest are immobilized at respectively different positions on the surface of the layer.

8. The detection device according to claim 5 or 6, characterized in that a treatment is applied to the surface so that only the substance of interest is immobilized on the surface of the layer.

9. A protein detection chip comprising: an organic electroluminescent device; and a layer existing between opposite electrodes of the organic electroluminescent device and having a surface on which a protein of interest is immobilized.

10. The protein detection chip according to claim 9, characterized in that the layer on which the protein of interest is immobilized is any one of a hole transport layer, an electron transport layer, a luminescent layer, a buffer layer, and an electrode layer in the organic electroluminescent device.

11. The protein detection chip according to claim 9 or 10, characterized in that at least two kinds of proteins of interest are immobilized at respectively different positions on the surface of the layer.

12. The protein detection chip according to claim 9 or 10, characterized in that a treatment is applied to the surface so that only the protein of interest is immobilized on the surface of the layer.

\* \* \* \* \*